United States Patent [19]

Hassler

[11] 4,095,597

[45] Jun. 20, 1978

[54] ARRANGEMENT FOR MEASURING CROSS-SECTIONAL FLUCTUATIONS OF CONDUITS STREAMED THROUGH BY FLUIDS AND FOR SUPPLYING INDICATIONS OF VOLUMETRIC FLOW AND/OR CONDUIT ELASTICITY BASED THEREON

[75] Inventor: Dieter Hassler, Erlangen, Germany

[73] Assignee: Siemens Aktiengesellschaft, Berlin & Munich, Germany

[21] Appl. No.: 661,247

[22] Filed: Feb. 25, 1976

[30] Foreign Application Priority Data

Mar. 5, 1975 Germany .............................. 2509568

[51] Int. Cl.[2] .............................................. A61B 5/02
[52] U.S. Cl. .................................. 128/205 Z; 73/602
[58] Field of Search ........................ 128/2.05 Z, 2 V; 73/194 R, 194 A, 194 E, 67.6, 602

[56] References Cited

U.S. PATENT DOCUMENTS

| 3,554,030 | 1/1971 | Peronneau ........................ 73/194 A |
| 3,675,192 | 7/1972 | Fahrbach .......................... 73/194 A |

*Primary Examiner*—William E. Kamm

*Attorney, Agent, or Firm*—Hill, Gross, Simpson, Van Santen, Steadman, Chiara & Simpson

[57] ABSTRACT

An arrangement for measuring cross-sectional fluctuations on conduits which are streamed through by fluids, particularly blood vessels, pursuant to the Ultrasound-Doppler method, through the utilization of an ultrasound transmitter-receiver system, a Doppler apparatus for determining the power or intensity of Doppler signals, as well as a dividing element for the obtained Doppler signal intensities. A single ultrasound transmitter-receiver is provided for the irradiation or projection of ultrasound into the liquid and for the receipt of the ultrasound reflected from the liquid, wherein an installation is associated with the Doppler apparatus for the formation of the intensity of the Doppler signal with on the one hand, the amplitude fluctuations, as well as, on the other hand, a timewise arithmetic median value of the intensity without material fluctuations, and in which the dividing element is connected to this installation for the purpose of forming the quotient from these intensities.

The arrangement utilizes such quotient in the provision of indications of volumetric flow and conduit elasticity.

4 Claims, 1 Drawing Figure

U.S. Patent  June 20, 1978  4,095,597
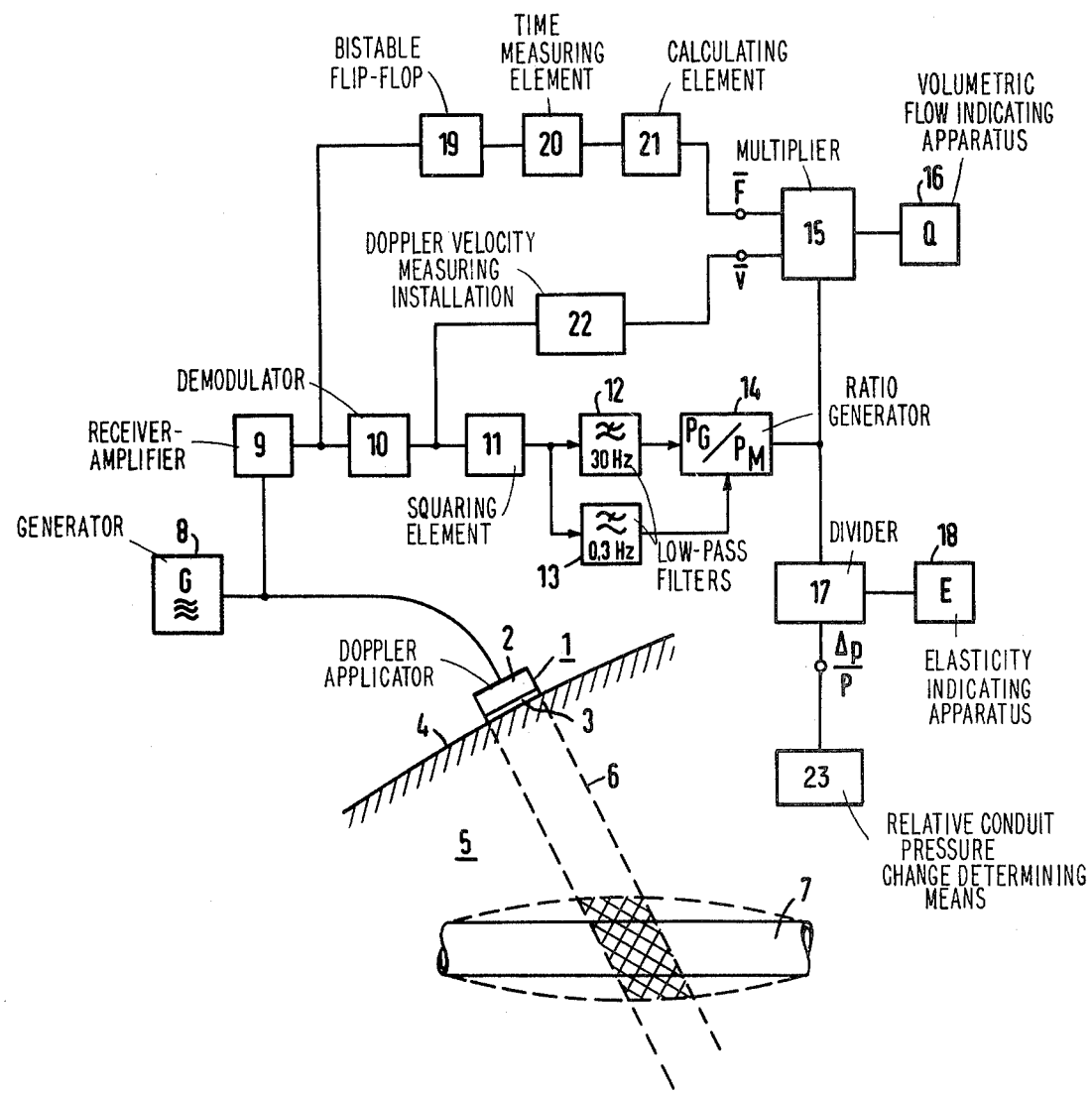

ARRANGEMENT FOR MEASURING CROSS-SECTIONAL FLUCTUATIONS OF CONDUITS STREAMED THROUGH BY FLUIDS AND FOR SUPPLYING INDICATIONS OF VOLUMETRIC FLOW AND/OR CONDUIT ELASTICITY BASED THEREON

FIELD OF THE INVENTION

The present invention relates to an arrangement for effecting measuring cross-sectional fluctuations on conduits which are streamed through by fluids, particularly blood vessels, pursuant to the Ultrasound-Doppler method, through the utilization of an ultrasound transmitter-receiver system, a Doppler apparatus for determining the power or intensity of Doppler signals, as well as a dividing element for the obtained Doppler signal intensities.

In the medical vessel diagnosis, cross-sectional measurements, for instance on blood vessels, serve in particular for the determination of the blood volume flow, as well as for the vein elasticity.

DISCUSSION OF THE PRIOR ART

As is known, the cross-sectional surface of blood vessels can be measured in that, by means of classical methods such as, for example, angiographs or ultrasound A-scan, there is determined the diameter of the vessel and, based on the assumption of a circular vessel cross-section, calculated therefrom the cross-sectional plane. However, the classical methods have the disadvantage in that the cross-section can merely be determined as a median value. Pulsations, however, are not determined along therewith, so that it is impossible to conduct a measurement of the phased blood flow, and also respectively an elasticity determination of the particular present vein.

An arrangement is already known through which the internal dimension of vessels can be continually determined by means of the Ultrasound-Doppler method. This arrangement encompasses a total of two predeterminately spaced, adjacent located ultrasound transmitter-receivers which concurrently project ultrasound against the vessel which is to be examined, for instance, a blood vessel, whereby the transmitting-receiving column of each transmitter-receiver widens considerably in the direction towards the vessel. The spacing between the two transmitter-receivers is hereby so selected that their transmitting-receiving columns overlap to some extent in the region of the targeted vessel, so that the transmitting-receiving column of one of the transmitter-receivers is just tangent with one side edge or boundary of the assumedly circular vessel and moreover passes completely through the vessel, whereas the transmitting-receiving column of the other transmitter-receiver cuts or intersects the vessel with the corresponding column boundary, thus only partially sounds the vessel through. Due to this differently strong sounding, at the outputs of a Doppler apparatus which is connected to the outputs of both transmitter-receivers, there are received correspondingly different Doppler signals intensities. From the relationship or ratio of the differingly strong Doppler signal intensities, for example, determined by means of a dividing element connected to the output of the Doppler apparatus with the aid of a calculator and in conjunction with further calculating magnitudes, such as the spacing between the two transmitter-receivers, as well as the aperture or generated angle between their transmitting-receiving columns, there can be computed the radius of the vessel at the sounded-through location pursuant to a predetermined mathematical formula. From the radius there can then be determined the circular cross-sectional plane of the vessel.

The above-mentioned known arrangement thus continually determines cross-sectional changes of a vessel so that in connection with the median value $\bar{v}$ of the flow velocity which, for example, is similarly obtained by means of the Ultrasound-Doppler method (for instance shown in U.S. Pat. No. 3,675,192), there is obtained a measure for the phasic blood flow. From the observation of the cross-sectional fluctuations there may be additionally obtained approximate information over the elasticity of the present vessel walls. Nevertheless, the arrangement is subject to two important disadvantages. On the one hand, it is technically extremely complex since, for effectuating the relatively complicated computing operations it is necessary to employ correspondingly complicated and expensive calculating elements. On the other hand, particularly with respect to volume flow or elasticity measurements, it is also quite unreliable in its measuring results since for the verification of the geometric assumptions such as, for example, circular vessel cross-section tangential contact of the vessel walls through the column boundary of the ultrasound column of the one transmitter-receiver and so forth, is frequently not possible in actual practice, or respectively difficult to maintain, and moreover for an extensively widening sounding field it is not possible to effect a targeting procedure and thereby also no filtering out of disruptive effects, for example, originating from also picked up neighboring vessels. Already obtained thereby are unavoidable measuring errors during determination of the cross-section even preceding the determining of the actual volumetric flow, and respectively also the vein elasticity, which will already falsify these values at this location.

SUMMARY OF THE INVENTION

Accordingly, it is an object of the present invention to provide an arrangement of this type for measuring cross-sectional fluctuations which in total eliminates the disadvantages encountered in the known measuring installations and which, with the smallest technical demands, provides a sufficiently precise measure for conduit cross-sections inclusive of their changes, and thereby also provides a basis for indications of the phasic volumetric flow, and respectively, the conduit elasticity.

The foregoing object is attained by means of an arrangement of the above-mentioned type in that, inventively, a single ultrasound transmitter-receiver is provided for the irradiation or projection of ultrasound into the liquid and for the receipt of the ultrasound reflected from the liquid, wherein an installation is associated with the Doppler apparatus for the formation of the intensity of the Doppler signal with on the one hand, the amplitude fluctuations, as well as, on the other hand, a timewise arithmetic median value of the intensity without material fluctuations and in which the dividing element is connected to this installation for the purpose of forming the quotient from these intensities.

With the lowest technical demand, the invention now facilitates the determination of the percentage fluctuation of a conduit cross-sectional plane. Hereby the fluctuations are accentuated in an enhanced measure in contrast with previous median cross-section indication, so that already due to this reason there can be obtained a more exact measure for the volumetric flow and the conduit elasticity. Since merely a single transmitter-receiver is provided, there are further obtained improved targeting capabilities, in particular at strongly collimated transmitting-receiving characteristics, and thereby also a signal receipt which is extensively freed from disruptions. Furthermore, the measurement is effected independently of the present form of the conduit cross-section so that prior imprecisions emanating from this direction cannot influence the measured results. Also not a problem is the influence of the proportionality constants between actual flow and the measured power or intensity on the total measured results. It is known that these proportionality constants, amongst others, are dependent upon the transmitted ultrasound energy, the receiving sensitivity of the ultrasound receiver, the ultrasound attenuation on the forward and return path, respectively, to and from the liquid, the energy loss through the dispersal at the liquid particles, and the magnitude of the signal recovery range. Inasmuch as, in lieu of two adjacently arranged transmitter-receivers, there is employed merely a single transmitter-receiver for effectuation of the measurement, there are obtained the same proportionality constants for the total power or intensity, as well as also for the arithmetic median value. During the subsequent intensity division there are thus accentuated the proportionality constants and thereby also the effect of the above-indicated influence magnitudes on the measurement.

Since the primary measured result is the percentage fluctuation of the current conduit cross-sectional plane, for determination of the total flow the relative change must be multiplied with the median value of the cross-section for example, classical, preferably through ultrasound A-scan, and with the median value of the flow velocity, so that preferably at the output of the power dividing elements there is connected a corresponding electronic multiplier element. The conduit elasticity, in contrast therewith, should preferably be obtained directly from the percentage fluctuation of the cross-sectional plane, for example in that the output signal of the power dividing element is divided in a further dividing element through a relative conduit pressure change which is measured, for example, by means of a collar, pressure probe or the like. For determination of the different Doppler signal intensities there should preferably be employed frequency filters which are set at different limiting frequencies, for example, for the blood flow measurement, one 30 Hz and one 0.3 Hz low-pass filter connected in parallel formation.

BRIEF DESCRIPTION OF THE DRAWING

Further advantages and details of the invention may now be ascertained from the following description of an exemplary embodiment thereof, taken in conjunction with the accompanying single FIGURE of the drawing illustrative of a schematic circuit block diagram of the invention.

DETAILED DESCRIPTION

In the single FIGURE, which shows an exemplary embodiment of the invention in a schematic representation, an Ultrasound-Doppler applicator is designated by reference numeral 1, and which encompasses a carrier portion 2, for example, constituted of plastic material, on whose application surface there is arranged an ultrasound vibrator 3 (thin piezoelectric metal plate). The vibrator 3 operates as an ultrasound-transmitter and receiver. In lieu of only one vibrator there may also be provided two thereof (for example, arranged immediately adjacent each other), of which one operates as a transmitter and the other one as a receiver.

The applicator 1 is so applied onto the body surface 4 of a patient for the purpose of blood flow measurement and, respectively, for the determination of the vein elasticity whereby the transmitting-receiving column 6 of the vibrator 3 fully encompasses a pulsating blood vessel 7 which is located in the tissue 5 below the skin 4.

The electrical control and, respectively, processing installation encompasses a high-frequency vibration generator 8, which, in transmitting rhythm with the vibrator 3, transmits high-frequency vibrations to the latter for excitation thereof. For the receipt of the ultrasound signals (echo signals) reflected by the streaming blood in the vessel 7, there serves a receiver-amplifier 9, having connected thereto a Doppler apparatus provided with a demodulator 10 for the demodulation of the received ultrasound impulses and with a power generator 11 (squaring element) for the formation of the Doppler signal intensity or power. Following the Doppler apparatus 10, 11 are two low-pass filters 12 and 13, of which the first filter 12, specially for blood flow measurement, evidences a limiting frequency of about 30 Hz and the second filter 13 a limiting frequency of about 0.3 Hz. The 30 Hz low-pass filter forms the Doppler signal intensity $P_G$ with amplitude fluctuations. The 0.3 Hz low-pass filter, in contrast therewith, determines a timewise arithmetic median value $P_M$ of the intensity without material fluctuations.

Both low-pass filters are connected on the output sides thereof to the two inputs of a power ratio generator 14 for the powers or intensities $P_G$ and $P_M$. Finally, connected to the output of this ratio generator 14 is multiplier element 15, as well as a divider element 17. The multiplier element 15 hereby multiplies the intensity ratio signal $P_G/P_M$ of the ratio generator 14 with the median cross-sectional value $\bar{F}$ of the vessel 7 and a median value $\bar{v}$ of the blood flow velocity. This product then represents the value of the blood volume flow at the measuring location in the blood vessel 7. Serving for indication of the volumetric flow value Q is an indicating apparatus 16. In contrast therewith, the divider elements 17 determines the quotient from the power ratio signal of the ratio generator 14 and a relative blood pressure change $\Delta P/P$, for example, obtained by means of a collar, pressure probe, or the like, indicated at 23. This quotient provides a measure for the vein elasticity E at the measuring location and can be indicated by means of an indicating apparatus 18.

The determination of the means cross-sectional value F in the above exemplary embodiment should preferably be effectuated by means of ultrasound A-scan which supplies two vessel wall-echo impulses as a measure for the median vessel diameter. For this purpose, the transmitter-receiver 1 pursuant to the FIGURE operates in an impulse operation, and an impulse-time interval measuring arrangement which is connected to the receiver amplifier 9, which in the usual manner can encompass, for example, a bistable flip-flop 19 (which responds to the successive vessel wall-echo impulses to produce an output impulse whose time duration is a measure of median vessel diameter) with a time measuring element 20 for measuring the duration of the output impulses of flip-flop 19, determines the time interval between the two vessel wall-echo impulses of the vessel 7 as a measure for the median vessel diameter $d$. Through recomputation in a calculating element 21 in accordance with the relationship $\bar{F} = \pi (d/2)^2$, there is then obtained the desired median cross-sectional value. The median value of the blood flow velocity $\bar{v}$, in contrast therewith, is obtained at the output of a Doppler velocity measuring installation 22 which is constructed, for example, in accordance with that shown in U.S. Pat. No. 3,675,192.

While there has been shown what is considered to be the preferred embodiment of the invention, it will be obvious that modifications may be made which come within the scope of the disclosure of the specification.

What is claimed is:

1. In a measuring arrangement comprising apparatus for measuring cross-sectional fluctuations of conduits streamed through by fluids, in particular blood vessels, pursuant to the Ultrasound-Doppler method, including an ultrasound transmitter-receiver system; a doppler apparatus for determining the intensity of the doppler signals; and a dividing element for the obtained doppler signal intensities, the improvement comprising: said transmitter-receiver system having a single ultrasound transmitter-receiver for projecting ultrasound into the fluid and for receiving the ultrasound reflected by the fluid; means being operatively connected to said doppler apparatus for forming the intensity of the doppler signals with amplitude fluctuations and the timewise arithmetic median value of the intensity without material fluctuations, said dividing element being connected to said means for forming a quotient of said intensities, as a measure of the fluctuation of conduit cross-sectional plane.

2. An arrangement as claimed in claim 1, said means comprising frequency filters set at different limiting frequencies for forming the different doppler signal intensities for said doppler signals, said frequency filters comprising two low-pass filters for blood flow measurements, a first one of said filters having a limiting frequency of about 30 Hz and the other filter having a limiting frequency of about 0.3 Hz.

3. An arrangement as claimed in claim 1, said arrangement further comprising apparatus for determining the volumetric flow of the fluid in said conduits comprising a multiplier element being connected to said dividing element, means for supplying to said multiplier element a median cross-sectional plane value and a median flow velocity value, said multiplier element multiplying the quotient signal of said dividing element with the median cross-sectional plane value and the median flow velocity value of the fluid.

4. An arrangement as claimed in claim 1, further comprising means for determining the relative conduit pressure change; and a second dividing element being connected to said first-mentioned dividing element forming the quotients of said intensity ratio signal and relative conduit pressure change so as to determine the conduit elasticity.

* * * * *